(12) United States Patent
Wiegert

(10) Patent No.: US 6,362,625 B1
(45) Date of Patent: Mar. 26, 2002

(54) ACTIVE MAGNETIC ANOMALY SENSING SYSTEM HAVING SYNCHRONIZED TRANSCEIVER AND DISCRIMINATOR

(75) Inventor: Roy F. Wiegert, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/533,437

(22) Filed: Mar. 23, 2000

(51) Int. Cl.[7] .............................. G01V 3/08; G01V 3/10; G01R 33/09; G01N 27/72
(52) U.S. Cl. ........................................ 324/329; 324/235
(58) Field of Search ................................ 324/326, 327, 324/320, 329, 235, 225, 239, 240, 241, 242, 243

(56) References Cited

U.S. PATENT DOCUMENTS 3,617,865 A * 11/1971 Hakata ........................ 344/326
3,978,396 A * 8/1976 Inouye et al. ............... 344/326

\* cited by examiner

Primary Examiner—Walter E. Snow
(74) Attorney, Agent, or Firm—Harvey A. Gilbert; Donald G. Peck

(57) ABSTRACT

An active magnetic anomaly sensing system includes a transmitter for transmitting a magnetic field towards a target. The magnetic field induces magnetic moments in the target which cause a magnetic anomaly field to propagate from the target. A first sensor positioned a distance D from the target directly senses magnetic field strength and produces a first output. A second sensor positioned a distance (D+d) from the target directly senses magnetic field strength and produces a second output. A controllable power supply is coupled to the transmitter for selectively activating and deactivating the transmitter. The first and second outputs are produced when the transmitter is deactivated. The second output is subtracted from the first output to generate a differential output indicative of the magnetic anomaly field propagating from the target. Means and methods are provided to synchronize the response characteristics of the sensors with one another, and to synchronize the transmitter with the sensors so that deactivation of the transmitter results in a near instantaneous detection of magnetic field transients by the sensors.

18 Claims, 4 Drawing Sheets

US 6,362,625 B1

ACTIVE MAGNETIC ANOMALY SENSING SYSTEM HAVING SYNCHRONIZED TRANSCEIVER AND DISCRIMINATOR

ORIGIN OF THE INVENTION

The invention described herein was made in the performance of official duties by an employee of the Department of the Navy and may be manufactured, used, licensed by or for the Government for any governmental purpose without payment of any royalties thereon.

FIELD OF THE INVENTION

The invention relates generally to magnetic sensors, and more particularly to a magnetic anomaly sensing system having a precision synchronized transceiver that directly measures magnetic field strength for improved detection and/or discrimination of targets.

BACKGROUND OF THE INVENTION

The basic construction of a prior art eddy-current-based active magnetic anomaly sensor system includes a transmitter and a receiver. The transmitter induces anomalous magnetic induction fields in an electrically conductive or magnetic target located in the sensor detection space. The receiver detects/discriminates the anomalous magnetic induction fields propagating from the target. The transmitter typically consists of electronic circuitry that drives a time dependent electrical current through an induction coil to generate a time and vector distance dependent magnetic induction field. The induction coil can be driven by a continuous wave or pulsed signal. When the generated magnetic induction field interacts with a target, anomalous magnetic moments are induced with in the target which, in turn, cause anomalous magnetic fields to propagate from the target. The sensor system's receiver typically consists of an induction or "search coil" sensor coupled to signal amplification and processing circuitry to condition and process the magnetic fields detected by the search coil. Through Faraday induction, the search coil generates a voltage proportional to the time derivative of the target's magnetic anomaly fields lying along the search coil's axis. Such sensor systems have a variety of shortcomings.

For portable active sensor systems having a transmitter and receiver in close proximity to one another, the spatial variation between the actively induced magnetic anomaly field and its time derivative at the receiver decreases with the inverse 6-th power of target-to-receiver distance. Accordingly, to double the detection range of a sensor system, transmitter amplitude or receiver sensitivity must be increased by a large factor, i.e., a factor of $25^6$ or 64. Also, relying on the time derivative of the magnetic anomaly field limits the sensor's time discrimination capability, receiver bandwidth and low frequency sensitivity.

Another shortcoming of prior art active magnetic anomaly sensing systems is the interference generated by the transmitter at the receiver. Since the transmitter drive fields are many orders of magnitude larger than the target's induced magnetic anomaly fields, the transmitted signal has a tendency to overwhelm or jam the reception of the much smaller magnetic anomaly fields. Even with specialized transmitter-receiver geometries, systems that use a continuous wave transmitter drive signal tend to lose much of a target's transient response. To combat this problem, pulsed transmitters are used and operate on the theory that reception occurs when the transmitter is off. While this works to a certain degree, time constant or transient effects of a typical transmitter coil last for tens of microseconds. Unfortunately, it is in this time frame that the strongest target-signature-related magnetic anomaly field transients are generated by the target. Thus, even though the transmitter coil is deactivated, coil transients tend to jam reception of the strongest magnetic anomaly fields. This problem precludes the use of prior art active magnetic anomaly sensing systems in the detection of non-conductive plastic mines in a conductive media (e.g., seawater) since plastic mines have an extremely short transient response.

Still another shortcoming of prior art active magnetic anomaly sensor systems stems from the use of inductive search coils as the magnetic anomaly field sensing element. Specifically, this type of sensing element responds primarily to the time derivative of magnetic flux change components that are parallel to the coil's axis. Therefore, the sensing element has limited spatial direction sensing capabilities for resolving the direction and magnitude of the three-dimensional vector components that comprise the magnetic anomaly field caused by the target. The lack of three-dimensional resolution limits the system's target localization and classification capabilities.

SUMMARY OF THE INVENTION

Accordingly, it is an object of the present invention to provide an active magnetic anomaly sensing method and system for sensing magnetic anomalies associated with a target when the target is subjected to a magnetic induction field.

Still another object of the present invention is to provide an active magnetic anomaly sensing system capable of directly detecting induced magnetic anomaly fields associated with a target.

Yet another object of the present invention is to provide an active magnetic anomaly sensing system that minimizes interference between the transmitter and receiver portions thereof.

A further object of the present invention is to provide an active magnetic anomaly sensing system capable of resolving a target-generated magnetic anomaly field in three dimensions.

A still further object of the present invention is to provide an active magnetic anomaly sensing system capable of detection, localization and classification of electrically non-conductive targets such as plastic mines immersed in conductive media such as seawater.

Other objects and advantages of the present invention will become more obvious hereinafter in the specification and drawings.

In accordance with the present invention, an active magnetic anomaly sensing system includes a transmitter for transmitting a magnetic field towards a target such that the magnetic field induces magnetic moments in the target which cause a magnetic anomaly field to propagate from the target.

A first (magnetoresistive) sensor is positioned a distance D from the target for directly sensing magnetic field strength and producing a first output indicative thereof. A second (magnetoresistive) sensor is positioned a distance (D+d) from the target for directly sensing magnetic field strength and producing a second output indicative thereof. A controllable power supply is coupled to the transmitter for selectively activating and deactivating the transmitter. The first output and second output are produced when the transmitter is deactivated. The second output is subtracted from the first output to generate a differential output indicative of the magnetic anomaly field propagating from the target. Means and methods are provided to synchronize the response characteristics of the sensors with one another, and to synchronize the transmitter with the sensors so that deactivation of the transmitter results in a near instantaneous detection of magnetic field transients by the sensors.

DETAILED DESCRIPTION OF THE INVENTION

Figure 1:
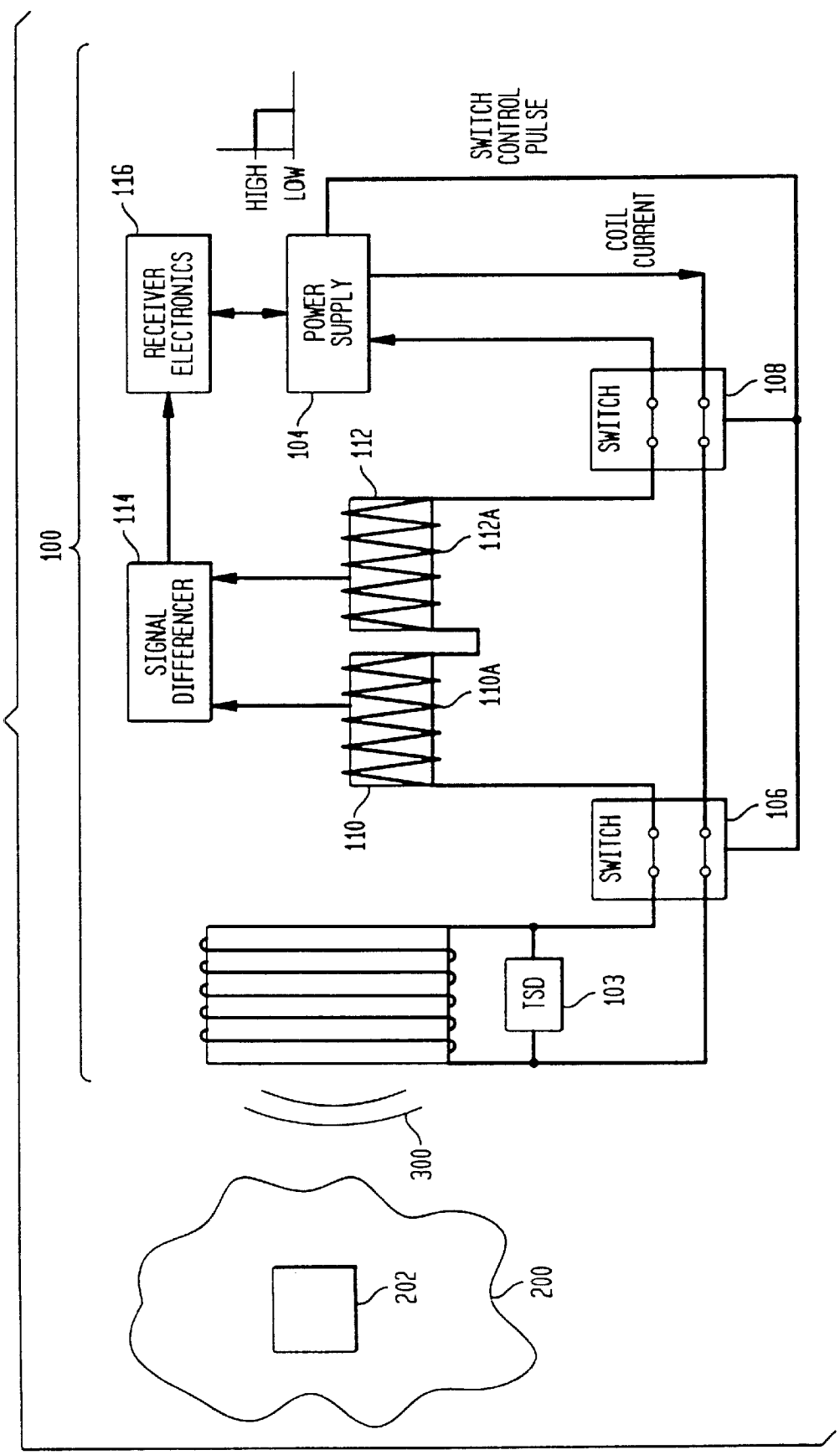
FIG. 1 is a schematic diagram of an embodiment of an active magnetic anomaly sensing system in its transmit mode in accordance with the present invention.
Figure 3:
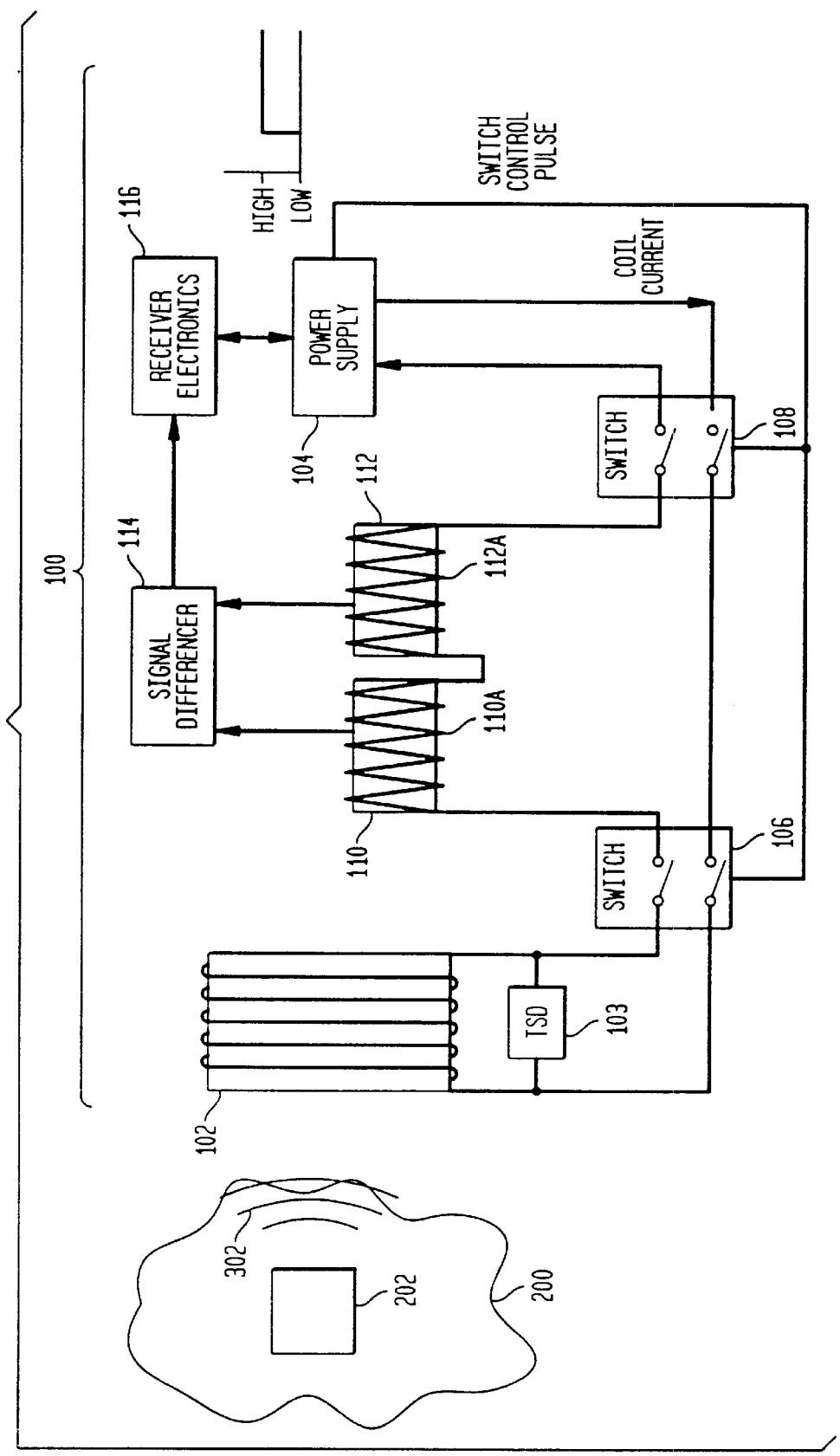
FIG. 3 is a schematic diagram of the active magnetic anomaly sensing system in its reception mode.

Referring now to the drawings, and more particularly to FIGS. 1 and 3, an embodiment of an active magnetic anomaly sensing system is shown and referenced generally by numeral 100. System 100 is configured in its transmit mode in FIG. 1 and in its reception mode in FIG. 3. Accordingly, like reference numerals are used for common elements in FIGS. 1 and 3.

System 100 can be used for the detection, localization and/or classification of a target 202 located in an area of interest 200. To be detectable, target 202 must either be made at least partially from electrically conductive or ferromagnetic materials, or be made from materials having a conductivity that is significantly different than that of the surrounding media. This criteria will be assumed for purposes of describing the present invention.

System 100 includes an inductive transmitter coil 102 capable of transmitting a magnetic field 300 towards area of interest 200 in which target 202 resides. In its preferred embodiment, transmitter coil 102 is constructed to provide an optimal combination of coil inductance, capacitance and electrical voltage breakdown immunity so that when a drive pulse is removed from coil 102, coil current drops to zero in less than one microsecond. Such a rapid current drop insures that the generated magnetic field 300 also falls to zero in less than one microsecond. As will be explained further below, this rapid cutoff response time minimizes interference at the receiver portion of system 100 and also allows for the detection of the rapid transient responses associated with, for example, plastic mines in seawater.

Transmitter coil 102 is driven by a power supply 104 capable of supplying a COIL CURRENT and a SWITCH CONTROL PULSE. Accordingly, power supply 104 is representative of one or more controllable current and/or voltage supply(ies) and associated electronics, specific designs of which are well known in the art and which are, therefore, not a limitation of the present invention.

In the transmit mode (FIG. 1), the COIL CURRENT from power supply 104 is supplied to transmitter coil 102 through closed serially connected solid state switches 106 and 108. A variety of solid state switches could be used in the present invention. One example of such a switch is the high current handling MOSFET switch model number Si4880DY manufactured by Vishay Siliconix, Santa Clara, Calif. Switches 106 and 108 close and remain closed during the HIGH portion of the SWITCH CONTROL PULSE received from power supply 104.

Figure 2A:
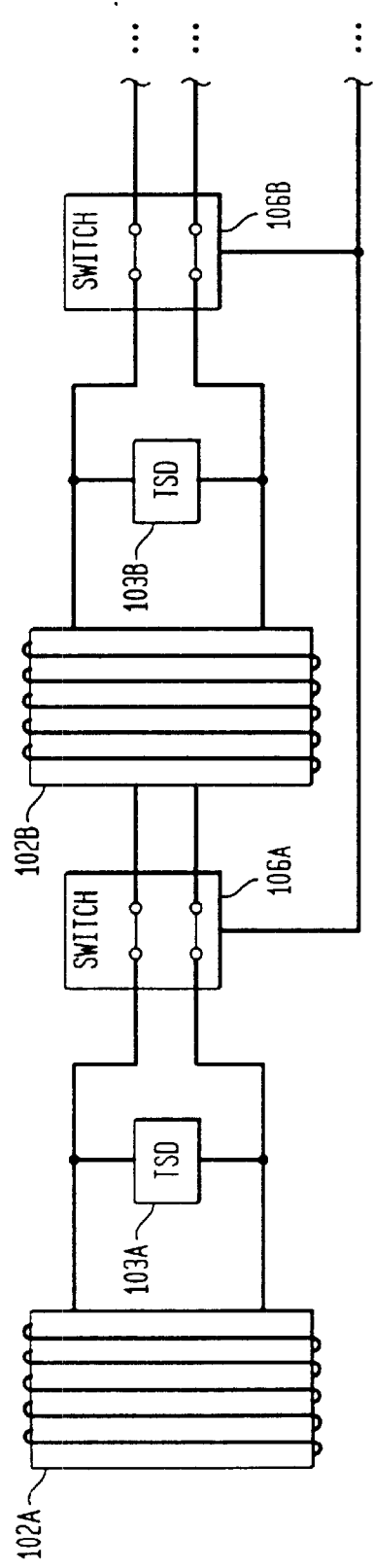
FIG. 2A is a schematic diagram of a segmented transmitter coil connected in series.
Figure 2B:
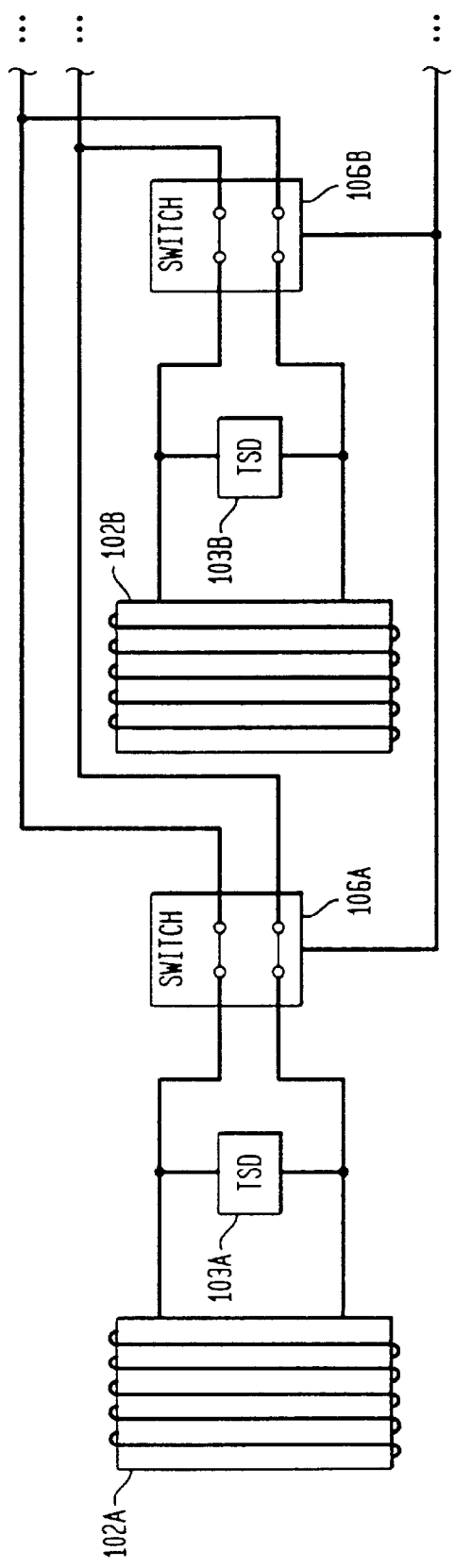
FIG. 2B is a schematic diagram of a segmented transmitter coil connected in parallel.

In the simplest approach to the problem of quickly cutting off magnetic field 300, transmitter coil 102 is a low inductance drive coil driven by a low drive current. A simple transient suppression device (TSD) 103 is coupled across the leads to transmitter coil 102. Solid state switches 106 and 108 must be able to withstand (with no leakage or breakdown current) the inductive "kick" voltage that is produced when the coil current is cut off. However, the switches may be limited in their ability to withstand the transients caused by the switching of large magnetic drive coils. Accordingly, for those applications requiring large magnetic moment drive coils, it may be necessary to use a multi-section transmitter coil configuration. Two such configurations are illustrated schematically in FIGS. 2A and 2B where the prefix numeral indicates the type of component (e.g., each 102 is indicative of a transmitter coil subsection, each 103 is a transient suppression device, etc.) and the suffix letter (e.g., A, B, etc.) indicates a subsection. In each case, the field outputs of the drive coil sections are additive thereby creating a transmit field similar to that of a single large drive coil. However, each coil subsection has its own set of switches with sufficient capacity to handle the subsections's switching transients. Transient suppression circuits and/or devices such as "snubbers" or varistors can be used to reduce the effect of inductive kick on the switches. The subsections could be connected in series (FIG. 2A) or in parallel (FIG. 2B). In either case, the coil subsections are physically located on the same coil form with transient suppression devices and switches physically located in close proximity to their coil.

System 100 also has receiver components that include identical magnetoresistive sensing elements 110 and 112, an electronic signal differencer 114 and receiver electronics 116. Magnetoresistive sensing element 110 detects a magnetic anomaly field 302 generated by target 202 as well as other background magnetic fields, while sensing element 112 is a reference sensor positioned to essentially only detect the background magnetic fields. As will be explained further below, sensing element 110 is located/positioned such that it will be closer to target 202 than sensing element 112.

Each of magnetoresistive sensing elements 110 and 112 has at least one ferromagnetic thin film element disposed along an axis. This is known as the field sensing axis. One or more field sensing axes can be defined by each sensing element 110 and 112. The resistance, and consequently the output voltage, of each thin-film element disposed along a field sensing axis changes as a function of magnetic field strength that is parallel thereto. When positioned in system 100, the field sensing axis of sensing element 110 is aligned parallel to the field sensing axis of sensing element 112. If each sensing element is a multi-axis sensing element, the corresponding field sensing axes of the two sensing elements are aligned parallel to one another.

A transceiver synchronization modality is provided by the following configuration. A polarity biasing coil 110A and 112A is either included with or coupled to sensing element 110 and 112, respectively. When energized, each of polarity biasing coils 110A and 112A causes its respective sensing element 110 and 112 to magnetically saturate along each field sensing axis to a selected polarity. Once saturated to a polarity, sensing elements 110 and 112 are poised to operate at their greatest possible sensitivity level when the saturating field is removed in the receiving mode. In terms of the illustrated embodiment, polarity biasing coils 110A and 112A must be able to handle the current load supplied to transmitter coil 102. This is because coils 110A and 112A are coupled in a series connection with transmitter coil 102 and power supply 104. That is, the COIL CURRENT supplied to transmitter coil 102 is also supplied to coils 110A and 112A when switches 106 and 108 are closed for the transmit mode illustrated in FIG. 1. Examples of magnetoresistive sensing elements that include high-current handling polarity biasing coils are the models HMC1001 and HMC1002 available from Honeywell Solid State Electronic Center, Plymouth, Minn. For the illustrated embodiment, if the polarity biasing coil does not exist or has low current handling capacity, auxiliary coils serving as coils 110A and 112A (or a circuit that can deliver a current within the coils capacity) would have to be provided.

The output signals generated by each of sensing elements 110 and 112 (in the reception mode) are supplied to signal differencer 114 to generate a difference signal. Accordingly, if sensing elements 110 and 112 are set to the same polarity (by their respective polarity biasing coil), signal differencer 114 is a subtraction circuit. Conversely, if sensing elements 110 and 112 are set to opposite polarities, signal differencer 114 could be a summing circuit. In either case, the difference signal is supplied to receiver electronics 116 which can include a variety of signal conditioning and processing elements (e.g., amplifiers, filters, A/D converters, processors, clocks, etc.). A variety of configurations of receiver electronics 116 would be well known to one of ordinary skill in the art and, as such, does not constitute a limitation of the present invention.

In operation, transmission of magnetic field 300 towards target 202 occurs when power supply 104 supplies the HIGH portion of the SWITCH CONTROL PULSE to switches 106 and 108, and the COIL CURRENT activates transmitter coil 102 through closed switches 106 and 108 as illustrated in FIG. 1. Simultaneously, the COIL CURRENT is supplied to polarity biasing coils 110A and 112A in order to synchronize the transceiver and set the polarity of sensing elements 110 and 112, respectively, while transmitter coil 102 is activated. During the reception mode of system 100 illustrated in FIG. 2, the LOW portion (e.g., zero) of the SWITCH CONTROL PULSE causes switches 106 and 108 to open. The opening of switches 106 and 108 in the illustrated embodiment causes the simultaneous deactivation of transmitter coil 102 and removal of biasing current from each of polarity biasing coils 110A and 112A. Since each of sensing elements 110 and 112 was magnetically saturated when the biasing current was removed, each of sensing elements 110 and 112 is synchronized to the same point of its response curve as the system switches from the transmit to the receive mode. Further, since each of elements 110 and 112 is saturated when the bias current is removed, each element is operating at its highest possible reception sensitivity within nanoseconds after transmitter coil 102 is deactivated. The outputs of sensing elements 110 and 112 are differenced at signal differencer 114 (as described above) and then processed by receiver electronics 116.

Figure 4:
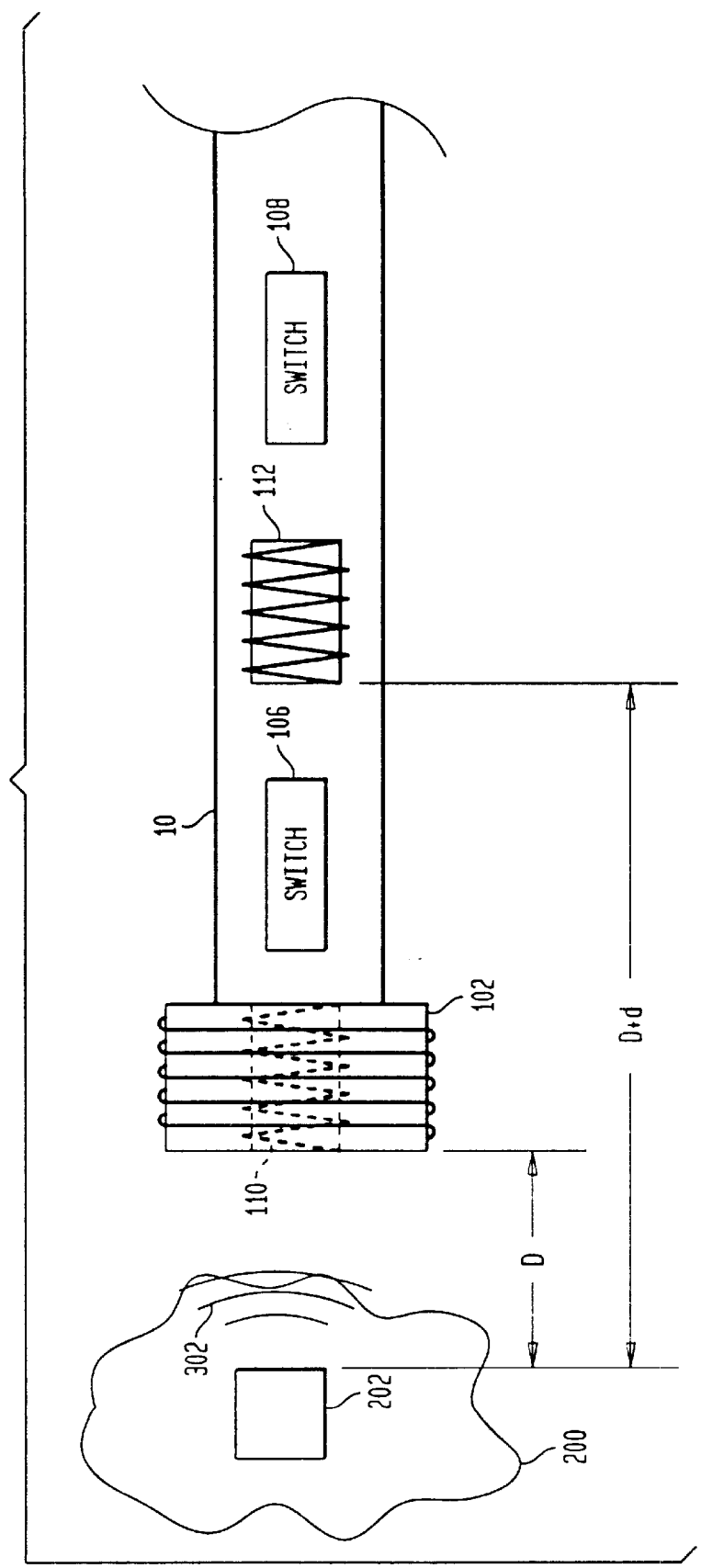
FIG. 4 is a schematic diagram of a construction configuration for the transmitter coil and sensing elements in the present invention.

As mentioned above, system 100 is configured such that sensing element 110 will be positioned closer to target 202 than sensing element 112. A possible construction illustrating this requirement is depicted schematically in FIG. 4 where transmitter coil 102 is mounted on the end of a rigid rod 10. Electrical connections between the elements are omitted for clarity of illustration. Mounted adjacent transmitter coil 102 (or within transmitter coil 102 for space saving reasons) is sensing element 110 such that a distance D separates sensing element 110 from target 202. Also mounted on rod 10 is sensing element 112 located a distance (D+d) from target 202. The field sensing axis(es) (not shown) of sensing element 112 is(are) aligned parallel to those of sensing element 110. The distance d between sensing elements 110 and 112 must be such that sensing element 112 detects very little of magnetic anomaly field 302 as compared with sensing element 110. That is, sensing element 110 detects magnetic anomaly field 302 along with all other surrounding magnetic fields, while sensing element 112 is positioned to detect only all other surrounding magnetic fields. In this way, when the outputs of sensing elements 110 and 112 are "differenced", only the magnetic anomaly field 302 due to target 202 will be processed by receiver electronics 116. The distance d between sensing elements 110 and 112 will vary depending on the active sensing application and sensitivity of the particular sensing element. Typically, the distance d will range from approximately 4 centimeters to approximately 1 meter. Also, note that solid state switches 106 and 108 can be mounted on rod 10 in close proximity to sensing elements 110 and 112, respectively, in order to minimize current transients when switches 106 and 108 are to be opened.

The advantages of the present invention are numerous. The unique application of magnetic induction drive coil and receiver synchronization, combined with the direct field sensing capabilities of magnetoresistive field sensing elements, provides a better system and method of active magnetic signal detection, localization and/or classification. By magnetically saturating the sensing elements during the transmission mode, the sensing elements are placed at their highest sensitivity for the reception mode. Further, since the reception mode is started at the same time the transmission mode is ended, the present invention is sensitive to the strongest and highest target information content magnetic anomaly field transients propagating from a target. The present invention's high-speed, synchronous transceiver response capability makes it well-suited to the problem of detecting non-conductive plastic mines in seawater.

When the sensor's transceiver (i.e., transmitter coil 102 and sensing elements 110/112) is moved so that a target is within the sensor's detection range, a signal is generated that can be used by the operator to home in on the target. Depending on the level of sophistication built in to its receiver electronics 116, the invention can be used as a relatively simple proximity detector that detects and localizes conductive objects. For more complex and critical tasks such as detection, localization and classification of explosive mines, the present invention's output can be used in a complex analysis of the temporal and spatial variations of target response in order to extract information about target geometry and composition. This information can be critical in the discrimination between real targets and background clutter. This present invention is applicable to a wide variety of commercial and military uses where its enhanced magneto-inductive target detection and discrimination capabilities can be used to provide more accurate and complete information about target characteristics.

Although the invention has been described relative to a specific embodiment thereof, there are numerous variations and modifications that will be readily apparent to those skilled in the art in light of the above teachings. For example, as mentioned above, the magnetoresistive field sensing elements could be constructed with thin-film elements disposed on multiple axes such as three orthogonal axes in order to make the sensing element sensitive to a magnetic anomaly field in three dimensions. Use of magnetoresistive sensing elements in this fashion is disclosed in U.S. Pat. No. 5,359,287. It is therefore to be understood that, within the scope of the appended claims, the invention may be practiced other than as specifically described.

What is claimed as new and desired to be secured by Letters Patent of the United States is:

1. An active magnetic anomaly sensing system, comprising:
   a transmitter for transmitting a magnetic field towards a target wherein said magnetic field induces magnetic moments in the target which cause a magnetic anomaly field to propagate from the target;
   a first sensor positioned a distance D from the target for directly sensing magnetic field strength and producing a first output indicative thereof;
   a second sensor positioned a distance (D+d) from the target for directly sensing magnetic field strength and producing a second output indicative thereof;
   a controllable power supply coupled to said transmitter for selectively activating and subsequently deactivating said transmitter; and
   means for subtracting said second output from said first output when said transmitter is deactivated to generate a differential output indicative of said magnetic anomaly field propagating from the target.

2. An active magnetic anomaly sensing system as in claim 1 wherein said transmitter includes a plurality of transmitter coils coupled in series.

3. An active magnetic anomaly sensing system as in claim 1 wherein said transmitter includes a plurality of transmitter coils coupled in parallel.

4. An active magnetic anomaly sensing system as in claim 1 wherein said first sensor comprises a first magnetoresistive field sensing element defining at least one first axis of magnetic field sensitivity and said second sensor comprises a second magnetoresistive field sensing element defining at least one second axis of magnetic field sensitivity, and wherein said first axis and said second axis are aligned parallel to one another.

5. An active magnetic anomaly sensing system as in claim 4 wherein said controllable power supply is coupled to said first magnetoresistive field sensing element and said second magnetoresistive field sensing element when said transmitter is activated in order to magnetically saturate each of said first magnetoresistive field sensing element and said second magnetoresistive field sensing element to a selected polarity, and wherein said controllable power supply is uncoupled from said first magnetoresistive field sensing element and said second magnetoresistive field sensing element when said transmitter is deactivated.

6. An active magnetic anomaly sensing system as in claim 4 wherein said distance d ranges between approximately 4 centimeters to approximately 1 meter.

7. An active magnetic anomaly sensing system, comprising:
   a transmitter for transmitting a magnetic field towards a target wherein said magnetic field induces magnetic moments in the target which cause a magnetic anomaly field to propagate from the target;
   a first magnetoresistive field sensing element (MFSE) positioned a distance D from the target for directly sensing magnetic field strength and producing a first output indicative thereof, said first MFSE having a first polarity biasing coil coupled thereto for magnetically saturating said first MFSE to a polarity when a biasing current is supplied thereto;
   a second magnetoresistive field sensing element (MFSE) positioned a distance (D+d) from the target for directly sensing magnetic field strength and producing a second output indicative thereof, said second MFSE having a second polarity biasing coil coupled thereto for magnetically saturating said second MFSE to said polarity when said biasing current is supplied thereto;
   each of said first MFSE and said second MFSE having at least one field sensing axis, wherein said at least one field sensing axis of said first MFSE is aligned parallel to said at least one field sensing axis of said second MFSE;
   a controllable power supply coupled to said transmitter, said first MFSE and said second MFSE, for selectively activating and deactivating said transmitter and for supplying said biasing current to said first polarity biasing coil and said second polarity biasing coil only when said transmitter is activated; and
   means for subtracting said second output from said first output to generate a differential output indicative of said magnetic anomaly field propagating from the target.

8. An active magnetic anomaly sensing system as in claim 7 wherein said transmitter includes a plurality of transmitter coils coupled in series.

9. An active magnetic anomaly sensing system as in claim 7 wherein said transmitter includes a plurality of transmitter coils coupled in parallel.

10. An active magnetic anomaly sensing system as in claim 7 wherein said distance d ranges between approximately 4 centimeters to approximately 1 meter.

11. An active magnetic anomaly sensing system as in claim 7 wherein said controllable power supply, said first polarity biasing coil, said second polarity biasing coil and said transmitter are connected in an electrical series, wherein said biasing current activates said transmitter.

12. A method of sensing magnetic anomalies, comprising the steps of:
   providing a transmitter capable of transmitting a magnetic field towards an area of interest;
   providing a first magnetoresistive field sensing element (MFSE) and a second magnetoresistive field sensing element (MFSE), each of said first MFSE and said second MFSE capable of directly sensing magnetic field strength, each of said first MFSE and said second MFSE having at least one field sensing axis, said first MFSE further having a first polarity biasing coil coupled thereto for magnetically saturating said first MFSE to a polarity when a biasing current is supplied thereto and said second MFSE having a second polarity biasing coil coupled thereto for magnetically saturating said second MFSE to said polarity when said biasing current is supplied thereto;
   positioning said first MFSE a distance D from said area of interest;
   positioning said second MFSE a distance (D+d) from said area of interest;
   aligning said at least one field sensing axes of said first MFSE and said second MFSE such that they are parallel to one another;
   activating said transmitter to transmit a magnetic field towards said area of interest wherein, if a target in said area of interest produces magnetic moments when subjected to said magnetic field, a magnetic anomaly field propagates from the target;

supplying, during said step of activating, said biasing current to said first polarity biasing coil and said second polarity biasing coil;

deactivating said transmitter;

removing, simultaneously with said step of deactivating, said biasing current from said first polarity biasing coil and said second polarity biasing coil, wherein said first MFSE generates a first output indicative of sensed magnetic field strength and said second MFSE generates a second output indicative of magnetic field strength; and subtracting said second output from said first output to generate a differential output indicative of said magnetic anomaly field propagating from the target.

13. A method according to claim 12 wherein said step of positioning said second MFSE includes the step of selecting said distance d to be in the range between approximately 4 centimeters to approximately 1 meter.

14. An active magnetic anomaly sensing system, comprising:

a transmitter for transmitting a magnetic field towards a target wherein said magnetic field induces magnetic moments in the target which cause a magnetic anomaly field to propagate from the target;

a first sensor positioned a distance D from the target for directly sensing magnetic field strength and producing a first output indicative thereof, said first sensor comprising a first magnetoresistive field sensing element defining at least one first axis of magnetic field sensitivity;

a second sensor positioned a distance (D+d) from the target for directly sensing magnetic field strength and producing a second output indicative thereof, said second sensor comprising a second magnetoresistive field sensing element defining at least one second axis of magnetic field sensitivity, wherein said first axis and said second axis are aligned parallel to one another;

a controllable power supply coupled to said transmitter for selectively activating and deactivating said transmitter wherein said first output and said second output are produced when said transmitter is deactivated; and means for subtracting said second output from said first output to generate a differential output indicative of said magnetic anomaly field propagating from the target.

15. An active magnetic anomaly sensing system as in claim 14 wherein said transmitter includes a plurality of transmitter coils coupled in series.

16. An active magnetic anomaly sensing system as in claim 14 wherein said transmitter includes a plurality of transmitter coils coupled in parallel.

17. An active magnetic anomaly sensing system as in claim 14 wherein said controllable power supply is coupled to said first magnetoresistive field sensing element and said second magnetoresistive field sensing element when said transmitter is activated in order to magnetically saturate each of said first magnetoresistive field sensing element and said second magnetoresistive field sensing element to a selected polarity, and wherein said controllable power supply is uncoupled from said first magnetoresistive field sensing element and said second magnetoresistive field sensing element when said transmitter is deactivated.

18. An active magnetic anomaly sensing system as in claim 14 wherein said distance d ranges between approximately 4 centimeters to approximately 1 meter.

* * * * *